United States Patent
Wang et al.

(10) Patent No.: US 7,904,253 B2
(45) Date of Patent: Mar. 8, 2011

(54) DETERMINATION OF CHEMICAL COMPOSITION AND ISOTOPE DISTRIBUTION WITH MASS SPECTROMETRY

(75) Inventors: Yongdong Wang, Wilton, CT (US); Ming Gu, Yardley, PA (US)

(73) Assignee: Cerno Bioscience LLC, Danbury, CT (US)

( * ) Notice: Subject to any disclaimer, the term of this patent is extended or adjusted under 35 U.S.C. 154(b) by 668 days.

(21) Appl. No.: 11/830,772

(22) Filed: Jul. 30, 2007

(65) Prior Publication Data

US 2008/0052011 A1 Feb. 28, 2008

Related U.S. Application Data (60) Provisional application No. 60/833,862, filed on Jul. 29, 2006.

(51) Int. Cl.
*G06F 19/00* (2006.01)

(52) U.S. Cl. .............. 702/27; 702/28; 702/85; 250/281; 250/282; 250/286; 250/424

(58) Field of Classification Search ............... 702/27, 702/28, 85; 250/281–282, 286, 424
See application file for complete search history.

(56) References Cited

U.S. PATENT DOCUMENTS

| | | | |
|---|---|---|---|
| 6,983,213 B2* | 1/2006 | Wang | 702/85 |
| 7,348,553 B2* | 3/2008 | Wang et al. | 250/282 |
| 7,451,052 B2* | 11/2008 | Wang et al. | 702/85 |

* cited by examiner

*Primary Examiner* — Drew A Dunn
*Assistant Examiner* — Hien X Vo
(74) *Attorney, Agent, or Firm* — David Aker (57) ABSTRACT

A method for determining elemental composition of ions from mass spectral data, comprising obtaining at least one mass measurement from mass spectral data; obtaining a search list of candidate elemental compositions whose exact masses fall within a given mass tolerance range from the accurate mass; reporting a probability measure based on a mass error; calculating an isotope pattern for each candidate elemental composition from the search list; constructing a peak component matrix including at least one of the isotope pattern and mass spectral data; performing a regression against at least one of isotope pattern, mass spectral data, and the peak component matrix; reporting a second probability measure for at least one candidate elemental composition based on the isotope pattern regression; and combining the two the probability measures into an overall probability measure. A method for determining elemental isotope ratios from mass spectral data.

54 Claims, 9 Drawing Sheets

| Accurate Mass (Da) | Calc Mass (Da) | Mass Error (mDa) | Mass Error (ppm) | DBE | Formula | Probability | $p_m$ value |
|---|---|---|---|---|---|---|---|
| 399.18055 | 399.1805 | -0.05 | -0.13 | 0.5 | C17 H38 O2 P3 S | 0.935 | 0.065 |
| | 399.1806 | 0.05 | 0.13 | 5.5 | C18 H32 N4 P S2 | 0.935 | 0.065 |
| | 399.1808 | 0.25 | 0.63 | 10.5 | C23 H27 O6 | 0.684 | 0.316 |
| | 399.1801 | -0.45 | -1.13 | 1.5 | C15 H31 N2 O8 S | 0.471 | 0.529 |
| | 399.1797 | -0.85 | -2.13 | 6.5 | C17 H28 N4 O5 P | 0.193 | 0.807 |
| | 399.1797 | -0.85 | -2.13 | 12.5 | C22 H24 N4 O2 Na | 0.193 | 0.807 |
| | 399.1814 | 0.85 | 2.13 | 1.5 | C15 H33 N2 O6 P2 | 0.193 | 0.807 |
| | 399.1814 | 0.85 | 2.13 | 7.5 | C20 H29 N2 O3 Na P | 0.193 | 0.807 |
| | 399.1816 | 1.05 | 2.63 | 9.5 | C24 H31 O S2 | 0.118 | 0.882 |
| | 399.1817 | 1.15 | 2.88 | 2.5 | C18 H32 O6 Na S | 0.092 | 0.908 |
| | 399.1793 | -1.25 | -3.13 | 0.5 | C17 H36 O4 P S2 | 0.072 | 0.928 |
| | 399.1792 | -1.35 | -3.38 | 6.5 | C22 H32 O Na S2 | 0.056 | 0.944 |
| | 399.1821 | 1.55 | 3.88 | 15.5 | C24 H23 N4 O2 | 0.034 | 0.966 |
| | 399.1789 | -1.65 | -4.13 | 5.5 | C19 H33 N2 O P2 S | 0.027 | 0.973 |
| | 399.1823 | 1.75 | 4.38 | 0.5 | C16 H37 N2 O P2 S2 | 0.021 | 0.979 |

FIG. 3

| Accurate Mass (Da) | Calc Mass (Da) | Mass Error (mDa) | Mass Error (ppm) | DBE | Formula | RMSE (Counts) | F-Value | p_i Value |
|---|---|---|---|---|---|---|---|---|
| 399.18055 | 399.1821 | 1.55 | 3.88 | 15.5 | C24 H23 N4 O2 | 0.42 | 3.0 | 0.67 |
| | 399.1808 | 0.25 | 0.63 | 10.5 | C23 H27 O6 | 0.79 | 10.8 | 0.81 |
| | 399.1797 | -0.85 | -2.13 | 12.5 | C22 H24 N4 O2 Na | 0.79 | 10.9 | 0.81 |
| | 399.1814 | 0.85 | 2.13 | 7.5 | C20 H29 N2 O3 Na P | 1.14 | 22.6 | 0.87 |
| | 399.1789 | -1.65 | -4.13 | 5.5 | C19 H33 N2 O P2 S | 1.22 | 25.8 | 0.88 |
| | 399.1792 | -1.35 | -3.38 | 6.5 | C22 H32 O Na S2 | 1.64 | 46.5 | 0.91 |
| | 399.1817 | 1.15 | 2.88 | 2.5 | C18 H32 O6 Na S | 1.64 | 46.9 | 0.91 |
| | 399.1806 | 0.05 | 0.13 | 5.5 | C18 H32 N4 P S2 | 1.68 | 48.9 | 0.91 |
| | 399.1816 | 1.05 | 2.63 | 9.5 | C24 H31 O S2 | 2.18 | 82.2 | 0.93 |
| | 399.1797 | -0.85 | -2.13 | 6.5 | C17 H28 N4 O5 P | 2.32 | 93.3 | 0.93 |
| | 399.1805 | -0.05 | -0.13 | 0.5 | C17 H38 O2 P3 S | 2.45 | 104.0 | 0.94 |
| | 399.1793 | -1.25 | -3.13 | 0.5 | C17 H36 O4 P S2 | 2.48 | 106.7 | 0.94 |
| | 399.1823 | 1.75 | 4.38 | 0.5 | C16 H37 N2 O P2 S2 | 2.55 | 113.2 | 0.94 |
| | 399.1801 | -0.45 | -1.13 | 1.5 | C15 H31 N2 O8 S | 2.98 | 153.8 | 0.95 |
| | 399.1814 | 0.85 | 2.13 | 1.5 | C15 H33 N2 O6 P2 | 3.41 | 201.6 | 0.96 |

FIG. 4

| Accurate Mass (Da) | Calc Mass (Da) | Mass Error (mDa) | Mass Error (ppm) | DBE | Formula | RMSE (Counts) | Combined p value |
|---|---|---|---|---|---|---|---|
| 399.18055 | 399.1805 | -0.05 | -0.13 | 0.5 | C17 H38 O2 P3 S | 1.68 | 0.06 |
| | 399.1806 | 0.05 | 0.13 | 5.5 | C18 H32 N4 P S2 | 2.45 | 0.06 |
| | 399.1808 | 0.25 | 0.63 | 10.5 | C23 H27 O6 | 0.79 | 0.26 |
| | 399.1801 | -0.45 | -1.13 | 1.5 | C15 H31 N2 O8 S | 2.98 | 0.50 |
| | 399.1821 | 1.55 | 3.88 | 15.5 | C24 H23 N4 O2 | 0.42 | 0.64 |
| | 399.1797 | -0.85 | -2.13 | 6.5 | C17 H28 N4 O5 P | 0.79 | 0.66 |
| | 399.1814 | 0.85 | 2.13 | 1.5 | C15 H33 N2 O6 P2 | 1.14 | 0.70 |
| | 399.1797 | -0.85 | -2.13 | 12.5 | C22 H24 N4 O2 Na | 2.32 | 0.75 |
| | 399.1814 | 0.85 | 2.13 | 7.5 | C20 H29 N2 O3 Na P | 3.41 | 0.77 |
| | 399.1816 | 1.05 | 2.63 | 9.5 | C24 H31 O S2 | 2.18 | 0.82 |
| | 399.1817 | 1.15 | 2.88 | 2.5 | C18 H32 O6 Na S | 1.64 | 0.82 |
| | 399.1789 | -1.65 | -4.13 | 5.5 | C19 H33 N2 O P2 S | 1.22 | 0.85 |
| | 399.1792 | -1.35 | -3.38 | 6.5 | C22 H32 O Na S2 | 1.64 | 0.86 |
| | 399.1793 | -1.25 | -3.13 | 0.5 | C17 H36 O4 P S2 | 2.48 | 0.87 |
| | 399.1823 | 1.75 | 4.38 | 0.5 | C16 H37 N2 O P2 S2 | 2.55 | 0.92 |

DETERMINATION OF CHEMICAL COMPOSITION AND ISOTOPE DISTRIBUTION WITH MASS SPECTROMETRY

This application claims priority, under 35 U.S.C. §119(e), from provisional patent application Ser. No. 60/833,862 filed on Jul. 29, 2006, which is hereby incorporated by reference in its entirety.

CROSS REFERENCE TO RELATED PATENT APPLICATIONS/PATENTS

The entire contents of the following documents are incorporated herein by reference in their entireties, for all purposes:
U.S. Pat. No. 6,983,213; International Patent Application PCT/US2004/013096, filed on Apr. 28, 2004; U.S. patent application Ser. No. 11/261,440, filed on Oct. 28, 2005; International Patent Application PCT/US2005/039186, filed on Oct. 28, 2005; and International Patent Application PCT/US2006/013723, filed on Apr. 11, 2006 and designating the United States of America as designated state; U.S. provisional patent Application Ser. No. 60/809,135; filed on May 26, 2006; and U.S. patent application Ser. No. 11/444,158; filed on May 30, 2006.

BACKGROUND OF THE INVENTION

1. Field of the Invention

The present invention relates to mass spectrometry systems. More particularly, it relates to mass spectrometry systems that are useful for the determination of elemental compositions or isotope distributions, including for large organic molecules such as proteins or peptides, environmental pollutants, pharmaceuticals and their metabolites, and petrochemical compounds, to methods of analysis used therein, and to a computer program product having computer code embodied therein for causing a computer, or a computer and a mass spectrometer in combination, to affect such determination.

2. Prior Art

It has been generally accepted by those skilled in the art that the determination of elemental composition using mass spectrometry requires high mass accuracy, which can only be expected from a higher resolution system, typically a qTOF, FTMS, or a similar system such as the newly introduced OrbiTrap system manufactured by Thermo Electron Corporation of Waltham, Mass., USA. The rationale behind high mass accuracy for the purpose of elemental composition determination is well established in the field. For example, an elemental composition search with C (0-50), H (0-100), N (0-5), O (0-10), S (0-2), P (0-3), and Na (0-1) in a small mass tolerance window of +/−0.002 Da for a small molecule compound at an accurately measured mass of 399.1806 Da will result in only about 15 possible formulas, a manageable list from which to narrow down and determine the correct elemental composition. More generally, it has been found that 5 ppm mass error would allow for the easy determination of elemental composition from small molecule drugs or metabolites to large molecule proteins or peptides.

In the crossed referenced patents and applications, such as U.S. Pat. No. 6,983,213, it has been shown that an extensive mass spectral calibration involving both mass and peak shape function can achieve high mass accuracy on even a unit mass resolution system, making elemental composition determination feasible on routine mass spectrometry systems. Furthermore, the advantages of performing elemental composition search using (preferably fully calibrated) profile mode mass spectral data have also been disclosed in the above cross referenced applications, particularly in International Patent Application PCT/US2004/013096, filed on Apr. 28, 2004; U.S. patent application Ser. No. 11/261,440, filed on Oct. 28, 2005; International Patent Application PCT/US2005/039186, filed on Oct. 28, 2005.

With both the accurate mass and the profile fitting information available, the list of candidate formulas from the elemental composition search can be ranked or scored based on either the mass error or the profile fitting error, creating some level of confusion.

In addition, as an important niche application of mass spectrometry, the measurement of isotope ratios is of key importance in many applications, including geology, identification of the source of origins for agricultural products, or even clinical diagnostics such as the determination of H-Pylori through breath $CO_2$ analysis. This is typically achieved on dedicated high resolution mass spectrometers such as magnetic sector instruments and referred to as the isotope ratio mass spectrometry or IRMS, after chemical derivatization of the target compound into a more measurable form such as $CO_2$.

SUMMARY OF THE INVENTION

It is an object of the invention to provide a mass spectrometry system and a method for operating a mass spectrometry system that provides a combined statistical measure for elemental composition search and a new mean for isotope distribution measurement, in accordance with the methods described herein.

It is another object of the invention, and has been realized to be highly desirable by the present inventors, to provide a statistically sound approach and combine the two prior art ranking or scoring systems described above into one based on the probability of a given formula being the correct one.

Also in accordance with the invention, the present inventors have realized that with the extensive mass spectral calibration involving both mass and peak shape function from the crossed referenced patents and applications, such as U.S. Pat. No. 6,983,213, it is possible to perform elemental composition analysis for the purpose of compound identification under the assumption that all elements involved have known isotope distribution such as one would typically expect from their natural abundances. If the compound is already known (and its elemental compositions defined), it is possible to treat the isotope distribution of a given element in the compound as unknowns to be determined, thus achieving isotope ratio determination in the original compound form (without chemical derivatization) on an ordinary mass spectrometry system such as a unit mass resolution quadrupole MS instrument.

It is yet another object of the invention to provide a storage media having thereon computer readable program code for causing a mass spectrometry system to perform the method in accordance with the invention.

An additional aspect of the invention is, in general, a computer readable medium having thereon computer readable code for use with a mass spectrometer system having a data analysis portion including a computer, the computer readable code being for causing the computer to analyze data by performing the methods described herein. The computer readable medium preferably further comprises computer readable code for causing the computer to perform at least one the specific methods described.

Of particular significance, the invention is also directed generally to a mass spectrometer system for analyzing chemical composition, the system including a mass spectrometer portion, and a data analysis system, the data analysis system operating by obtaining calibrated continuum spectral data by processing raw spectral data; generally in accordance with the methods described herein. The data analysis portion may be configured to operate in accordance with the specifics of these methods. Preferably the mass spectrometer system further comprises a sample preparation portion for preparing samples to be analyzed, and a sample separation portion for performing an initial separation of samples to be analyzed. The separation portion may comprise at least one of an electrophoresis apparatus, a chemical affinity chip, or a chromatograph for separating the sample into various components.

BRIEF DESCRIPTION OF THE DRAWINGS

The foregoing aspects and other features of the present invention are explained in the following description, taken in connection with the accompanying drawings, wherein.

DETAILED DESCRIPTION OF THE PREFERRED EMBODIMENTS

Figure 1:
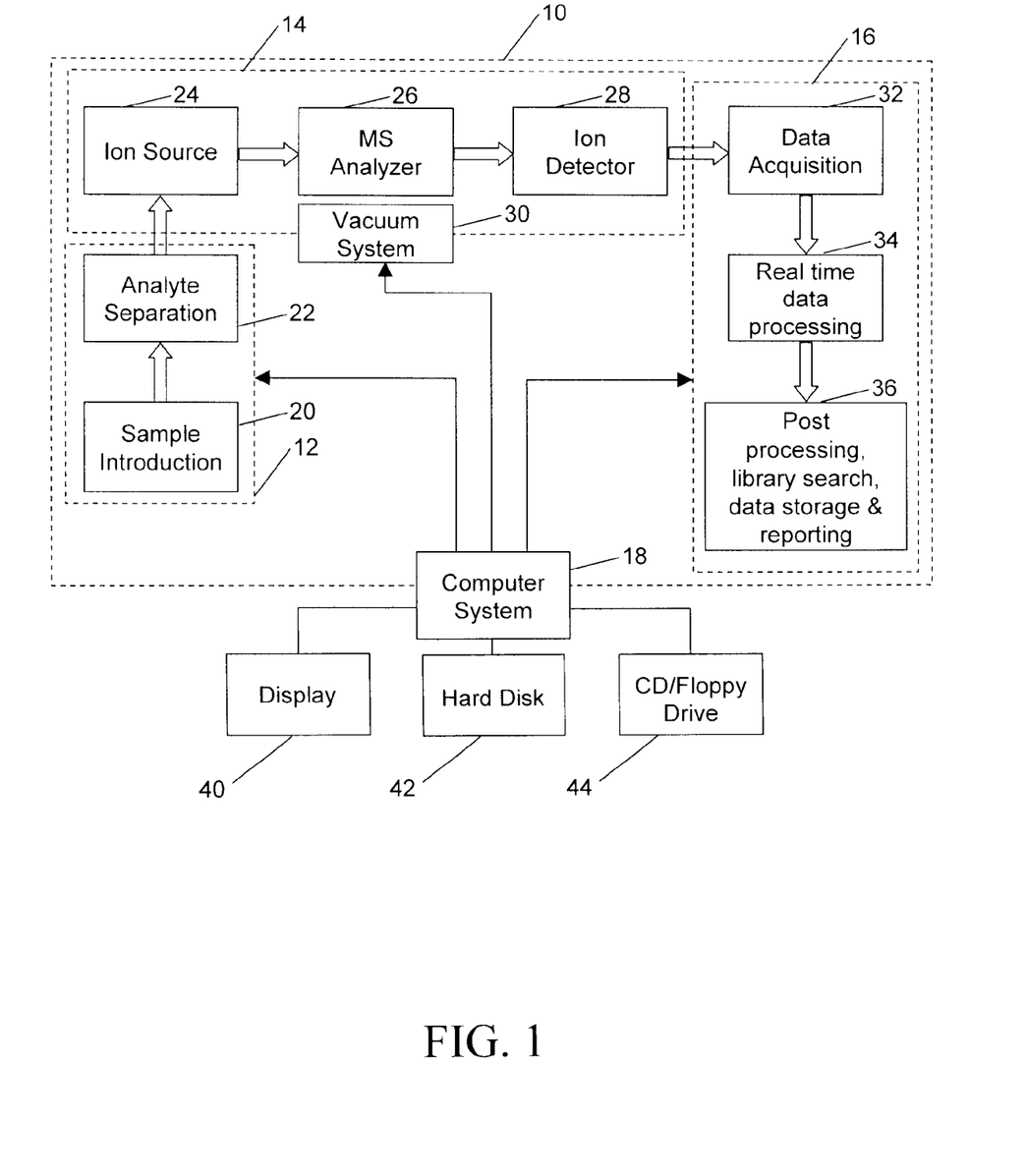
FIG. 1 is a block diagram of a mass spectrometer in accordance with the invention.

Referring to FIG. 1, there is shown a block diagram of an analysis system 10, that may be used to analyze drugs or other molecules, as noted above, incorporating features of the present invention. Although the present invention will be described with reference to the embodiments shown in the drawings, it should be understood that the present invention can be embodied in many alternate forms of embodiments. In addition, any suitable types of components could be used.

Analysis system 10 has a sample preparation portion 12, a mass spectrometer portion 14, a data analysis system 16, and a computer system 18. The sample preparation portion 12 may include a sample introduction unit 20, of the type that introduces a sample containing proteins or peptides of interest to system 10, such as Finnegan LCQ Deca XP Max, manufactured by Thermo Electron Corporation of Waltham, Mass., USA. The sample preparation portion 12 may also include an analyte separation unit 22, which is used to perform a preliminary separation of analytes, such as the proteins to be analyzed by system 10. Analyte separation unit 22 may be any one of a chromatography column, an electrophoresis separation unit, such as a gel-based separation unit manufactured by Bio-Rad Laboratories, Inc. of Hercules, Calif., and is well known in the art. In general, a voltage is applied to the unit to cause the proteins to be separated as a function of one or more variables, such as migration speed through a capillary tube, isoelectric focusing point (Hannesh, S. M., *Electrophoresis* 21, 1202-1209 (2000), or by mass (one dimensional separation)) or by more than one of these variables such as by isoelectric focusing and by mass. An example of the latter is known as two dimensional electrophoresis.

The mass spectrometer portion 14 may be a conventional mass spectrometer and may be any one available, but is preferably one of MALDI-TOF, quadrupole MS, ion trap MS, qTOF, TOF/TOF, or FTMS. If it has a MALDI or electrospray ionization ion source, such ion source may also provide for sample input to the mass spectrometer portion 14. In general, mass spectrometer portion 14 may include an ion source 24, a mass analyzer 26 for separating ions generated by ion source 24 by mass to charge ratio, an ion detector portion 28 for detecting the ions from mass analyzer 26, and a vacuum system 30 for maintaining a sufficient vacuum for mass spectrometer portion 14 to operate efficiently. If mass spectrometer portion 14 is an ion mobility spectrometer, generally no vacuum system is needed and the data generated are typically called a plasmagram instead of a mass spectrum.

The data analysis system 16 includes a data acquisition portion 32, which may include one or a series of analog to digital converters (not shown) for converting signals from ion detector portion 28 into digital data. This digital data is provided to a real time data processing portion 34, which process the digital data through operations such as summing and/or averaging. A post processing portion 36 may be used to do additional processing of the data from real time data processing portion 34, including library searches, data storage and data reporting.

Computer system 18 provides control of sample preparation portion 12, mass spectrometer portion 14, and data analysis system 16, in the manner described below. Computer system 18 may have a conventional computer monitor 40 to allow for the entry of data on appropriate screen displays, and for the display of the results of the analyses performed. Computer system 18 may be based on any appropriate personal computer, operating for example with a Windows® or UNIX® operating system, or any other appropriate operating system. Computer system 18 will typically have a hard drive 42, on which the operating system and the program for performing the data analysis described below is stored. A drive 44 for accepting a CD or floppy disk is used to load the program in accordance with the invention on to computer system 18. The program for controlling sample preparation portion 12 and mass spectrometer portion 14 will typically be downloaded as firmware for these portions of system 10. Data analysis system 16 may be a program written to implement the processing steps discussed below, in any of several programming languages such as C++, JAVA or Visual Basic.

For a given mass spectrum, the following basic model can be constructed:

$$r = Kc + e \qquad \text{Equation 1}$$

where r is an (n×1) matrix of the profile mode mass spectral data measured of the sample, digitized at n m/z values; c is a (p×1) matrix of regression coefficients which are representative of the concentrations of p ions or fragments in the sample; K is an (n×p) matrix composed of profile mode mass spectral responses for the p components, all sampled at the same n m/z points as r; and e is an (n×1) matrix of a fitting residual with contributions from random noise and any systematic deviations from this model.

The components arranged in the columns of matrix K will be referred to as peak components, which may optionally include any baseline of known functionality such as a column of 1's for a flat baseline or an arithmetic series for a sloping baseline. A key peak component in the matrix K is the known mass spectral response for the candidate ion or fragment, which can be theoretically calculated.

Figure 3:
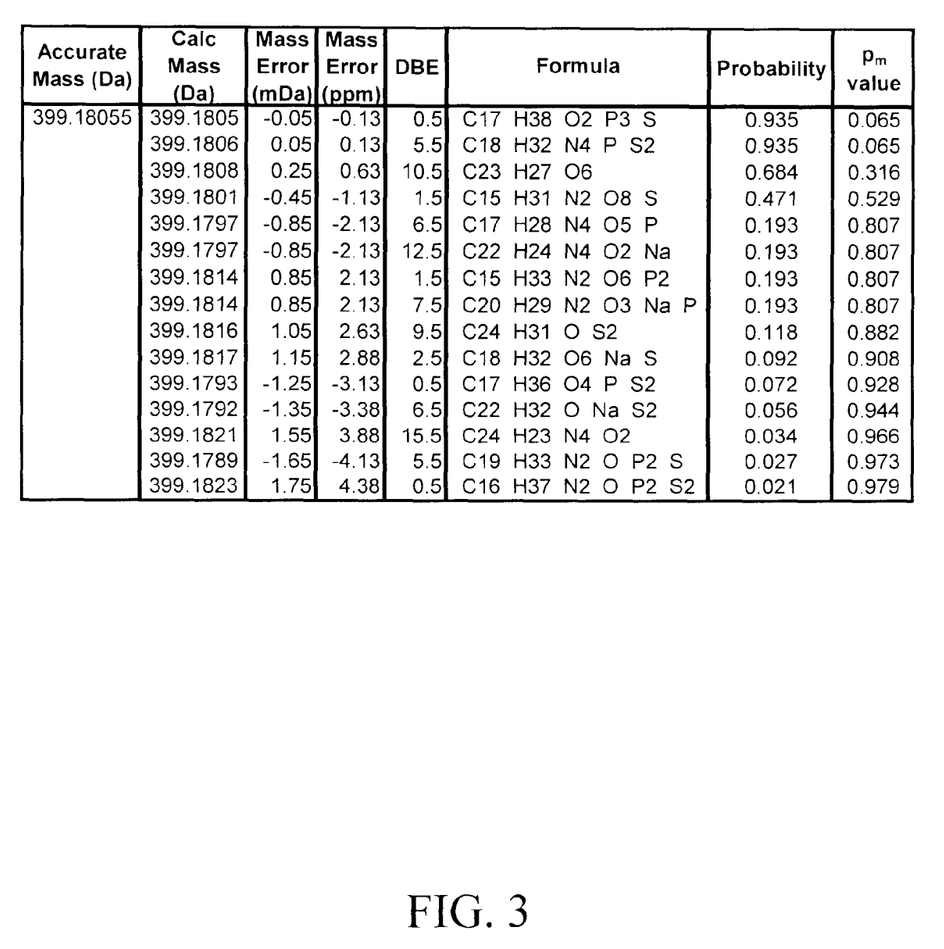
FIG. 3 is a list of candidate formulas ranked by a probability measure related to mass error.

The candidate ion or fragment comes from a list of possible elemental compositions obtained through a search with accurately measured monoisotopic mass within a mass tolerance window. The user will typically perform an accurate mass measurement on the monoisotopic mass and then specify a list of possible elements such as C, H, N, O, S, P, etc and the possible element number range for each. The user may optionally specify other constraints such as a range of double bond equivalent (DBE) and the specific nitrogen rule (odd electrons, even electrons, or both). These and other aspects of elemental composition and their chemistry constraints are well established in the open literature, e.g., Gross, R. A., *Chemical Educator* 8, 13-14 (2003). A list of all possible elemental compositions or formulas can be readily found that satisfy all these constraints including the accurate mass and mass tolerance range, a capability widely available on commercial systems such as the XCalibur software from Thermo Electron Corporation of Waltham, Mass., USA. FIG. 3 shows a list of 15 possible formulas obtained with the accurate mass of 399.18055 Da in the mass tolerance window of +/−0.0020 Da with C (0-50), H (0-100), N (0-5), 0 (0-10), S (0-2), P (0-3), and Na (0-1), sorted by the absolute mass error between the measured mass ($m_0$) and the theoretically calculated mass (m) for the corresponding candidate formula.

When the statistical distribution of the accurate mass measurement is known, the mass tolerance specified for the formula search can be established to reflect a high probability that the intended formula will be included in the given mass range. In the above example shown in FIG. 3, one accurate mass measurement m can be obtained for each or a group of mass spectral scan(s) containing the ion of interest and a standard deviation $s_m$ of 0.0059 Da can be calculated from 8 consecutive (a group of) scans. Based on the t-distribution, a mass tolerance window of +/−0.0020 Da would have a calculable confidence of including the correct ion in the given mass range of 399.1806±0.0020 Da through $$t^* = |m - m_0|/s_m = 0.0020/0.0059 = 3.39$$

A double-sided t-test with degrees of freedom df=8−1=7 gives a confidence level of 98.84%, or a p-value of $$p[|t(df)| > t^*] = 1 - 98.84\% = 0.0116.$$

The t-distribution, p-value and degrees of freedom df are all described by John Neter et al., in *Applied Linear Regression*, 2$^{nd}$ Ed., Irwin, 1989, p. 8, p. 12, and p. 7, the entire disclosure of which is incorporated by reference herein.

In addition, the absolute mass error used in the above ranking can be similarly converted into a statistically meaningful probability measure for better interpretation, using the same t-distribution with df=7, $$t = |m - m_0|/s_m$$

one can report the probability measure as $$p[|t(df)| > t^*]$$

or the p-value as $$p_m = p[|t(df)| < t^*]$$

The last 2 columns in FIG. 3 list both probability and p-value corresponding to each formula on the list.

This search and ranking based on mass error alone reflect only how well the monoisotopic mass of a candidate ion matches that of the measured accurate mass, which can lead to the wrong formula being selected even at a very high mass accuracy shown in FIG. 3. What is at least equally important is the match in their complete MS profiles including all isotopes and their relative abundances. The difference in MS profiles including all isotopes and their relative abundances between one candidate ion and the other is however quite subtle, typically at a few percent of the total intensity, unless a Cl or a Br element is involved, which typically display pronounced difference in their MS profiles. In order to take advantage of the MS profile difference at such a subtle level, it is imperative to include mass spectral peak shape function in the calculation. Otherwise, the mass spectral peak shape variation from one instrument to another and from one point in time to another overwhelms any subtle difference in MS profiles between two candidate formulas, significantly reducing the effectiveness of MS profile information, if not rendering it virtually useless, for most applications.

For each candidate formula thus identified, it is preferred that the peak component in matrix K be calculated as the convolution of the theoretical isotope distribution and the known mass spectral peak shape function. The theoretical isotope distribution can be calculated based on well known procedures outlined in U.S. Pat. No. 6,983,213 and International Patent Application PCT/US2004/034618 filed on Oct. 20, 2004. The known mass spectral peak shape function may be directly measured from a section of the mass spectral data, mathematically calculated from actual measurements through deconvolution, or given by the target peak shape function if a comprehensive mass spectral calibration has already been applied, all using the approach outlined in U.S. Pat. No. 6,983,213 and International Patent Application PCT/US2004/034618 filed on Oct. 20, 2004.

It should be noted that there is no need to perform any baseline correction on the actual measured mass spectral data in r or K as any difference in baseline between a peak component in K and the sample measurement in r will be fully compensated for by the baseline components also included in K.

It should also be noted that a peak component included in K does not have to include just one candidate formula or ion but could include multiple candidate formulas, or multiple ions, to account for a mass spectral response r that has contributions from these sources.

Optionally, one or more first derivatives corresponding to that of a peak component, a known linear combination of several peak components, or the measured mass spectral data r may be added into the peak components matrix K to account for any relative mass spectral errors between r and K. This ability to correct for systematic mass shift between measured and theoretical masses can make elemental composition determination more robust and simple in practice. For example, it is typically widely practiced in the art of high mass accuracy work for internal standards to be measured along with the unknown ions in order to correct for any small mass drift over time. Due to the capability of the current invention disclosed herein to compensate for mass drift numerically, here through the inclusion of derivative terms, it is now possible to perform elemental composition determination without the use of internal standards, simplifying the tedious process of introducing internal standards and avoiding losing the valuable measurement time spent on the internal standard ions and any associated contaminations or ion suppressions. Another important and practical application of numerical compensation for mass shift is to avoid space charge effects in ion-trap or FT-ICR cells. In these environments, the mass axis for a given ion can be shifted by a different amount depending on the other ions co-existing in the ion trap or cell and thus may change unpredictably over the course of a chromatographic run where different ions are eluted at different points in time. This well known effect has plagued ion traps and ICR cells for many years, making elemental composition determination on these instruments a challenge.

As an additional option for numerically compensating mass shift, either the measured mass spectrum r or the theoretically calculated peak components in matrix K can be adjusted with some elaborately added mass shift in an iterative fashion to minimize the error term e in Equation 1. These deliberate addition of shifts can be used in combination with numerically compensating the mass shift to achieve either more efficient computation or help compensating larger mass shift when numerically compensating the mass shift becomes a challenge due to the inaccuracies in Taylor series expansion, as pointed out in the cross-referenced U.S. Pat. No. 6,983,213, even with iterative improvement.

Once proper peak components are arranged into the matrix K, including any known interfering ions and labeled isotopes if applicable, the model above can be solved for concentration vector c for a given mass spectral response r, in a regression process, $$c = K^+ r \qquad \text{Equation 2}$$

where $K^+$ is a form of the inverse of K, which can, for example, take the form of:

$$K^+ = (K^T K)^{-1} K^T$$

as a least squares solution, as described by John Neter et al., in *Applied Linear Regression*, 2$^{nd}$ Ed., Irwin, 1989, p. 206, the entire disclosure of which is incorporated by reference herein. It should be noted that some variations can be utilized in setting up equations 1 and 2 and the solution to the concentration vector c, for computational reasons. For example, it may be computational advantageous to switch the calibrated mass spectral response r and the theoretically calculated mass spectral response containing the isotope pattern of a given candidate formula, i.e., construct a peak component matrix K using the calibrated mass spectral response r, its 1$^{st}$ derivative, and other known interfering ions or baselines, and treat the theoretically calculated mass spectral response for a given candidate formula as r in above regression analysis. This way, the pseudo-inverse $K^+$ only needs to be calculated once and applicable to all candidate formulas, making it computationally more desirable when the number of candidate formulas runs into the thousands with significant dimensions on K matrix.

The concentration vector c contains the concentration information of all included peak components including any baseline contribution automatically determined. For derivatives included, the corresponding coefficients in concentration vector c contain the relative mass error information for the given components included in the peak component matrix, as outlined in the cross-referenced U.S. Pat. No. 6,983,213 and International Patent Application PCT/US2004/034618 filed on Oct. 20, 2004.

For most mass spectrometry applications where the noise in the mass spectral response r typically comes from ion shot noise, it is advantageous to use weighted regression in the above model where the weight at each mass sampling point would be inversely proportional to the signal variance at this mass spectral sampling point, i.e., the mass spectral intensity in r. This is further described by John Neter et al., in *Applied Linear Regression*, 2$^{nd}$ Ed., Irwin, 1989, p. 418, the entire disclosure of which is incorporated by reference herein.

In addition to the estimated c from Equation 2, which contains quantitative information critical for quantitative analysis, there is other equally important qualitative information that can be derived from the mass spectral data r or regression residual e through the same regression analysis, such as the statistical significance level for each peak component in K through a t-statistic measure, $$t^* = c_i / s_i \qquad \text{Equation 3}$$

where $s_i$ is the standard deviation estimate for a particular peak component i in its concentration estimate $c_i$, all using the approach outlined in U.S. Pat. No. 6,983,213 and International Patent Application PCT/US2004/034618 filed on Oct. 20, 2004.

For this t-statistic, a p-value can be defined as the probability that a non-existing ion with expected concentration of zero could have by chance generated a high enough signal with the t value given in Equation 3, or, $$p[t(df) > t^*] \qquad \text{Equation 4}$$

i.e., the false positive probability for this ion or fragment. In Equation 4, as in other notations before, t(df) is the t distribution of the concentration estimate at given degrees of freedom df. Typically, the higher the t-statistic in Equation 3, the smaller the p-value, and the more likely this ion or fragment of a given elemental composition (formula) exists.

To measure the match between measured MS profile and that generated from each candidate formula from a list such as the one shown in FIG. 3, a regression analysis using the above described approach is performed to generate a p-value, $p_i$, based on this MS profile match, to further refine the elemental composition search, as outlined in the cross referenced International Patent Application PCT/US2004/013096, filed on Apr. 28, 2004, U.S. patent application Ser. No. 11/261,440, filed on Oct. 28, 2005, and International Patent Application PCT/US2005/039186, filed on Oct. 28, 2005. The t-values thus generated relates to the question of whether a particular formula could significantly account for the measured signal, which in many cases tend to have large values indicating a high degree of statistical significance for all candidate formulas and losing the necessary differentiation power.

Instead of using the t-test as stated above, an F-test can be used to generate a statistic which compares the RMSE (Root-Mean Squared Error, calculated from residual term e in Equation 1) for a given candidate formula to the RMSE from the actual random error in the measured mass spectral profile data. The latter RMSE can, for example, be calculated by subtracting a smoothed version of the profile data r, $r_0$, from r itself to produce a new residual $e_1$, $$e_1 = r - r_0$$

from which a $RMSE_1$ can be calculated. This random vector $e_1$ can also be established directly through duplicate measurements or repeated MS scans. An F-statistic can be calculated as $$F^* = RMSE^2 / RMSE_1^2$$

The $F^*$ value and the corresponding p-value, $p_i$, measures the significance of using a particular formula in the regression to drive the residual towards true random error level, and therefore be more relevant in differentiating one formula from the other.

Figure 4:
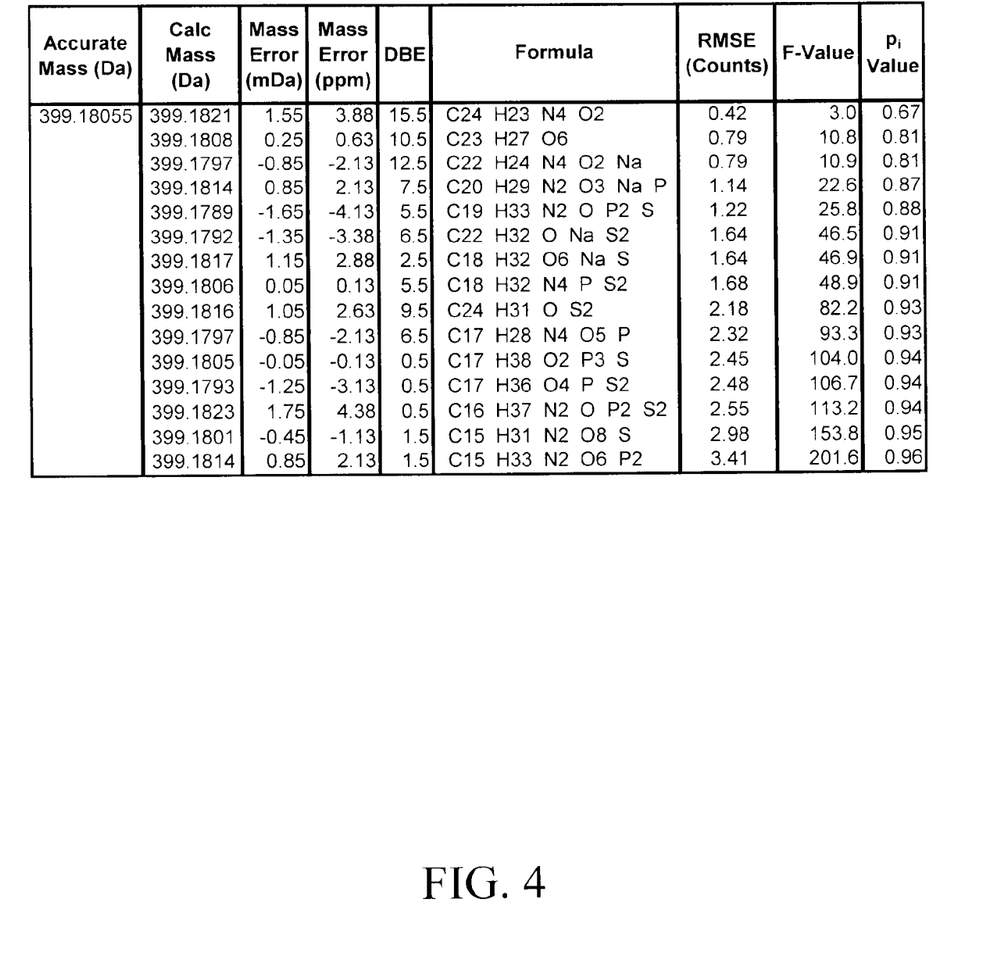
FIG. 4 is a list of candidate formulas ranked by a probability measure related to MS profile regression.

FIG. 4 shows a refined search list based on and sorted by the p-value thus calculated. Comparing FIGS. 3 and 4, it becomes immediately clear that what matches the best in terms of monoisotopic mass does not necessarily match best in terms of MS profile, and vice versa. For example, FIG. 4 indicates that the formula $C_{24}H_{23}N_4O_2$ with the mass error of −1.50 mDa is actually the top hit rather than the original top hit of $C_{18}H_{32}N_4PS_2$ with only 0.05 mDa mass error. How to merge these two search lists and combine the two different probability measures, $p_m$ and $p_i$, into a statistically sound overall probability measure p for easy interpretation, is one key aspect of this invention to be described below.

Figure 5:
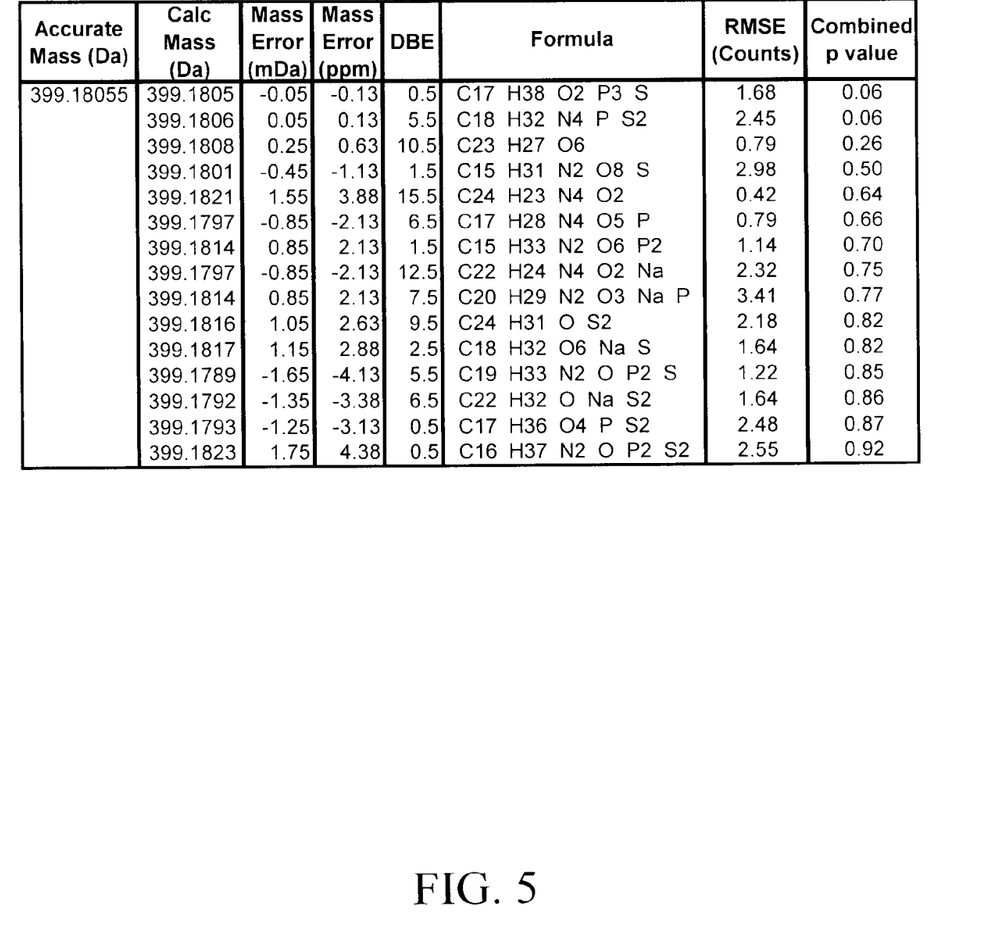
FIG. 5 is a list of candidate formulas ranked by the combined probability measure derived from both mass error and MS profile regression.

Since $p_m$ and $p_i$ represent two independent probability measures, both in terms of false positive rate, a combined p-value can then be easily constructed as:

$$p = p_m p_i \quad \text{Equation 5}$$

which will provide an overall probability for each formula on the search as 1-p. FIG. 5 is now sorted with the overall p-value.

The benefit of combining accurate mass search with MS profile regression can now be seen immediately where the overall p-value or false positive probability can be drastically reduced due to the multiplication of two small p-values $p_m$ and $p_i$.

When more than one ion is involved in the peak component matrix K, and some of these involved ions turn out not to be statistically significant, the steps from Equation 1 to 5 can be repeated with insignificant ions deleted from matrix K in the analysis, as outlined in the cross referenced U.S. Pat. No. 6,983,213; International Patent Application PCT/US2004/013096, filed on Apr. 28, 2004; U.S. patent application Ser. No. 11/261,440, filed on Oct. 28, 2005; International Patent Application PCT/US2005/039186, filed on Oct. 28, 2005; and International Patent Application PCT/US2006/013723, filed on Apr. 11, 2006; U.S. provisional patent application 60/809,135, filed on May 26, 2006; and U.S. patent application Ser. No. 11/444,158, filed on May 30, 2006.

Compared to other alternatives currently in use or being proposed, this approach represents a new and fast approach to MS analysis with significant advantages:

a. Due to its sound mathematical and statistical basis, this approach eliminates the many ad hoc and nonlinear operations in current mass spectral processing and elemental composition searching, resulting in a theoretically elegant process for the elemental composition search.

b. By working with all known and significant isotopes from candidate formulas, complete data integrity is preserved with all isotope patterns automatically included in the analysis or search.

c. Instead of ad hoc scoring, statistically rigorous confidence level such as t-statistics, F-statistics or the respective p-values can be established for a given formula to rank possible candidates for elemental composition search.

Thus, this approach provides an easy, fast, yet mathematically sound and statistically rigorous measure for elemental composition search.

Figure 2:
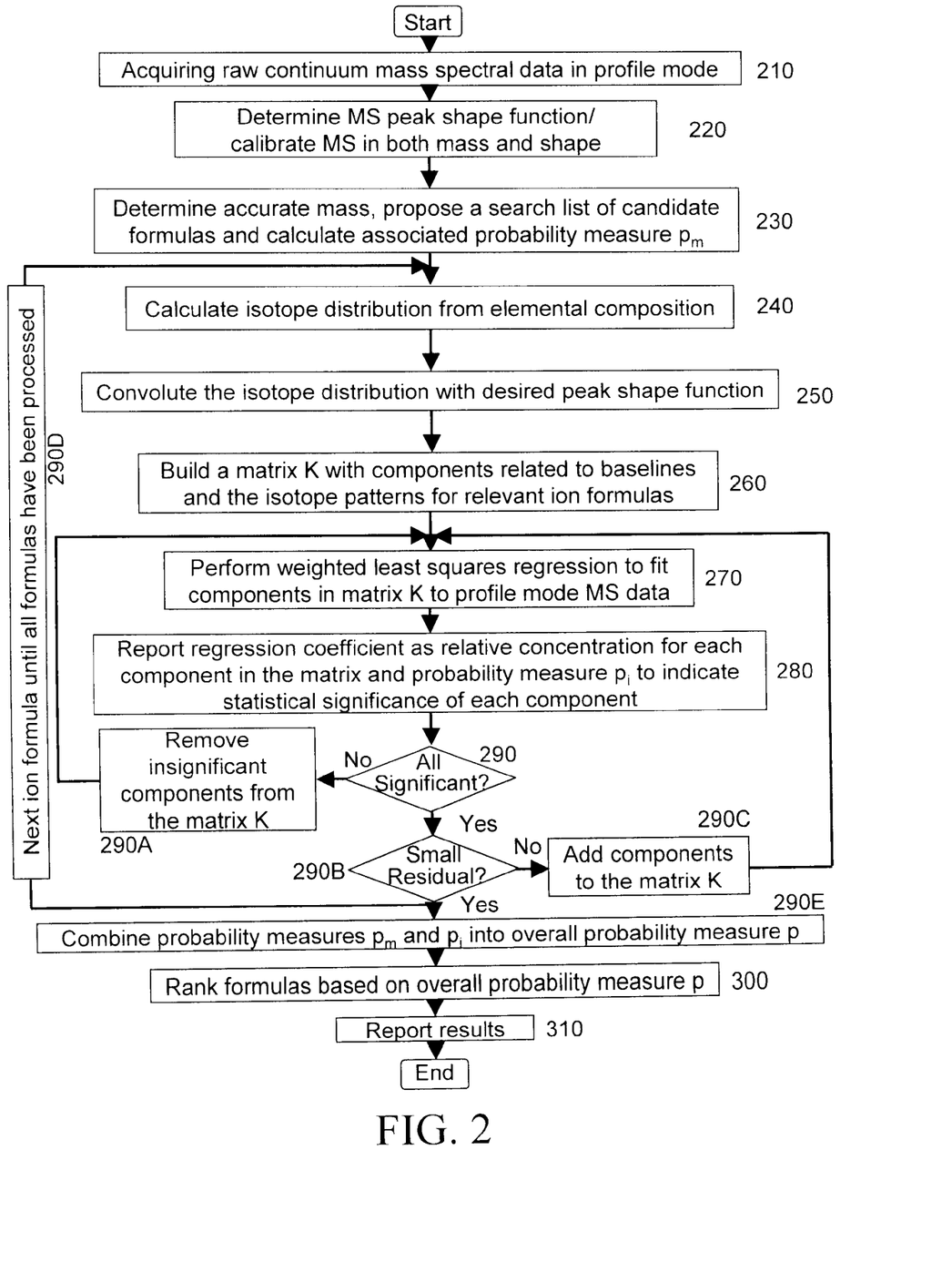
FIG. 2 is one possible flow chart of the steps in the analysis used by the system of FIG. 1.

Referring to FIG. 2, at step 210, raw continuum mass spectral data is obtained for a sample containing the analyte of interest. While, as mentioned above, most commercial techniques utilize stick spectral data, it will be recognized that the use of the profile mode raw spectrum means that data is not lost due to a premature gross simplification of the features of the data. However, this raw spectrum has characteristics relating to instrument peak shape function, instrument resolution, and baseline variations due to spurious ions and neutral particles that may reach the detector. Further, there may be a mass dependence with respect to all of these potential factors. For example, there is an exponential decay of baseline displacement as a function of increasing m/z in a MALDI system, principally due to ions of the matrix material, some of which arrive at the detector, despite every attempt to reduce their presence.

At step 220, the raw data acquired in step 210 is subjected to a full calibration of the mass spectrometer based on internal and/or external standards so as to standardize the raw continuum data. This assures that the peaks are lined up at the proper m/z values, and that the shape of the peaks is properly defined and known mathematically. This is preferably accomplished by the procedure set forth in U.S. Pat. No. 6,983,213 and International Patent Application PCT/US2004/034618 filed on Oct. 20, 2004, the entire contents of which are incorporated herein by reference. Instead of a full mass spectral calibration, the peak shape function can be calculated and used in the following mass spectral search process, at the expense of reduced mass accuracy during the search.

At step 230, the accurate mass for the ion of interest is reported from its monoisotopic or other isotope peak. It is noted that the reported accurate mass for a peak other than the monoisotopic peak is the weighted average of all isobars falling within the peak with weights equal to their relative abundances, a unique feature of the peak detection process outlined in the cross referenced U.S. Pat. No. 6,983,213 and International Patent Application PCT/US2004/034618 filed on Oct. 20, 2004. Using accurate mass other than the monoisotopic mass has the advantage of potentially avoiding saturation-induced systematic mass error on the monoisotopic peak, especially in time-of-flight (TOF) instruments. Based on the accurate mass reported, a list of candidate formulas can be selected and proposed whose exact masses match the reported accurate mass with a given mass tolerance window. The candidate formulas can be selected by giving a list of possible elements and their possible element number range (lower and upper bound), some chemistry constraints such as double bond equivalence (DBE)/nitrogen rule, and a mass tolerance which can be a multiple of estimated standard deviation corresponding to a given confidence level. For each candidate formula, an exact mass can be calculated and compared to the reported accurate mass to produce a mass error, which can be translated into a probability measure such as a p-value, $p_m$, for the given formula. Similar to the reported accurate mass for isotope peaks other than the monoisotopic peak, the corresponding exact mass will be calculated as the weighted average of all isobars within the same peak.

At step 240, a theoretically calculated isotope distribution can be obtained for each candidate formula on the list. This can be taken into account in the manner described in U.S. Pat. No. 6,983,213 and International Patent Application PCT/US2004/034618 filed on Oct. 20, 2004.

At step 250 the isotope distribution is convoluted with the peak shape function calculated or specified as the target peak shape function in the full mass spectral calibration, all given in step 220, to obtain a calculated isotope pattern (mass spectral continuum) for the candidate formula. As used herein, for this purpose, and for other purposes throughout this document, the term convolution may refer to matrix operations, or point by point operation in Fourier transform space, or any other type of convolution, filtering, or correlation, either of a traditional type, or not.

At step 260, a matrix K is generated to include known and sometime mass-dependent baseline functions and the isotope pattern for the candidate formula. Examples of possible baseline functions include a flat line and several lower order terms such as linear or quadratic terms. The combination of these lower order terms can adequately compensate for an exponentially decaying baseline within a small mass spectral range, and help arrive at the computationally efficient linear solutions in step 270, though one may choose to incorporate the nonlinear terms explicitly and seek a nonlinear solution instead. Matrix K may optionally contain any other components interfering with the candidate's isotope pattern such as the isotope patterns from co-existing ions including isotope labeled version of the same candidate ion or a measured mass spectral background taken prior to and/or after the chromatographic peak of interest. To model the possible mass offset between r and components in K, the first derivatives of the components in K or the first derivative of the sample measurement r may also be included.

At step 270, a weighted least squares regression is performed to fit the components of the matrix generated in step 260 to the acquired and/or calibrated mass spectral spectrum data of step 220, in the form given in Equations 1-2.

At step 280, the regression coefficients (values in c) are reported out as the relative concentrations for components included in matrix K along with probability measures in the form of F-statistic, t-statistic or p-value for example, given in Equations 3-4.

At step 290 a statistical test based on t-statistic, p-value, or other measures such as F-statistic is performed to determine whether any or all of components included in the matrix K are significant. In this regard, the baseline may be treated in the analysis as if it is another compound found in the sample (in the data produced in step 220). If any component is insignificant, then branching to step 290A occurs, and this component is removed from the matrix K before the next iteration back to step 270 (and continuing on to steps 280 and 290). This process of first estimating the contribution of the possible components as part of an overall fit, followed by the removal of insignificant baseline components serves the purpose of unbiased correction of components including baselines without unnecessarily introducing extra components into matrix K and Equation 1. Typically as more components are added to the matrix K, its conditioning would get worse, resulting in less precise estimation of concentrations and a worsening of other statistical confidence. However, by removing insignificant components in the process, the conditioning of the K matrix is improved, leading to more precise concentration estimates for c and higher statistical confidence. This iterative removal of some components at this point is optional.

When all insignificant components have been removed, at step 290B, a statistical test on the residual e (Equation 1) is performed to check and see if there are other components missing in the matrix K resulting in larger than expected residuals, in which case more components may be added in step 290C before returning to step 270 for another iteration. These components may be an isotope labeled version of the candidate ion involved, or may be another ion not separated in retention time and mass during an LC/MS experiment, or a general background from the sample matrix, which can be included by isolating a retention time region prior to and/or after the chromatographic peak of interest.

When all components are deemed significant with statistically insignificant residuals, branching is through step 290D and a return to step 240 for the analysis of the next candidate formula. When all candidate formulas have been analyzed, the individual probability measures pertaining to each candidate can be combined to form an overall probability measure in step 290E. Equation 5 above shows an example of how to progress from individual p-values to an overall p-value.

These overall probability measures can be used to rank all candidate formulas in step 300 and to report this as analysis or search results in step 310.

These probability measures are reported out by computer 18 (FIG. 1) by being displayed on the monitor 40 and/or by printing on a printer (not shown) associated with computer 18.

Figure 6A:
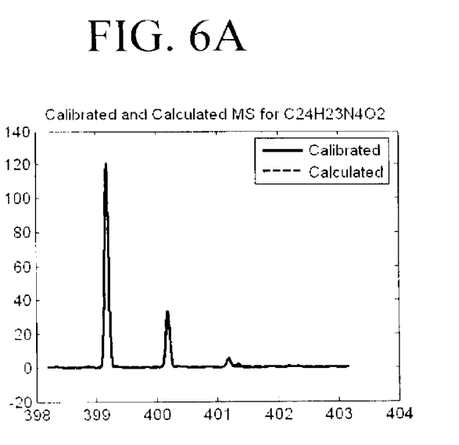
FIGS. 6A, 6B, 6C and 6D are graphs showing the spectral match between the calibrated MS profile and those from the two top candidates in FIG. 5.
Figure 6B:
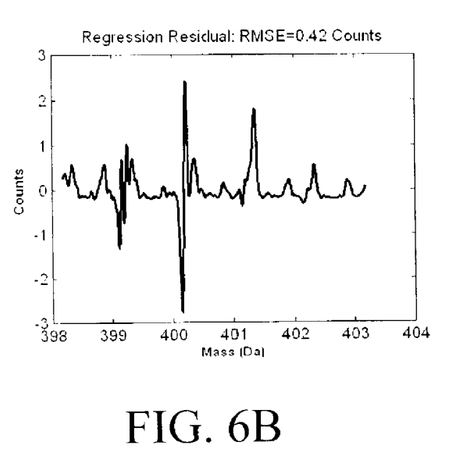
Figure 6C:
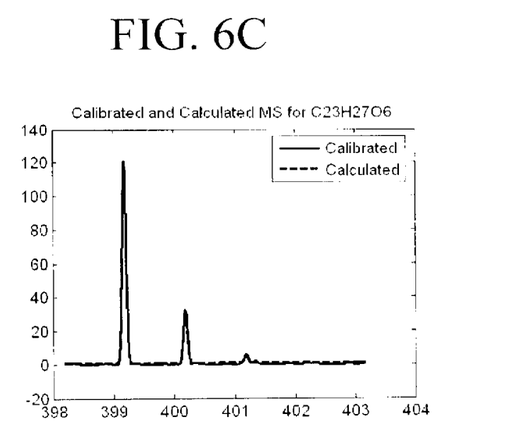
Figure 6D:
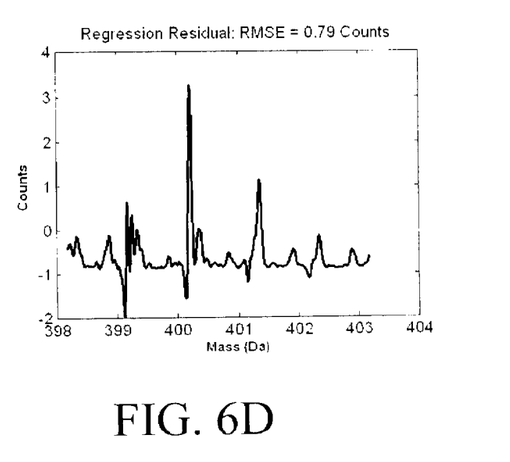
Figure 7A:
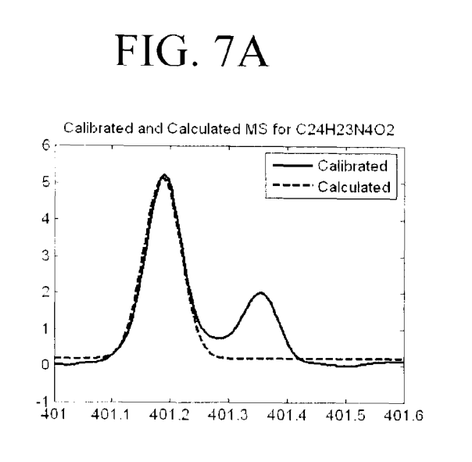
FIGS. 7A, 7B, 7C and 7D are graphs showing zoomed-in versions of FIGS. 6A, 6B, 6C and 6D, respectively.
Figure 7B:
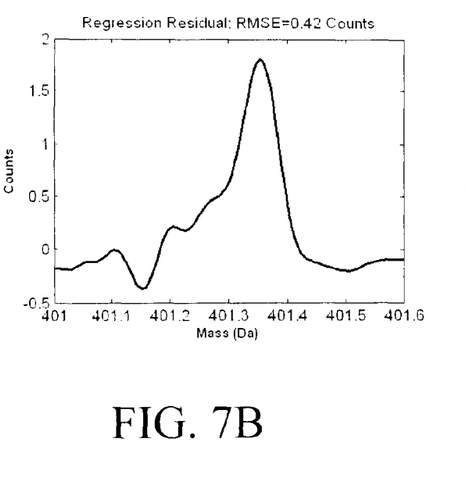
Figure 7C:
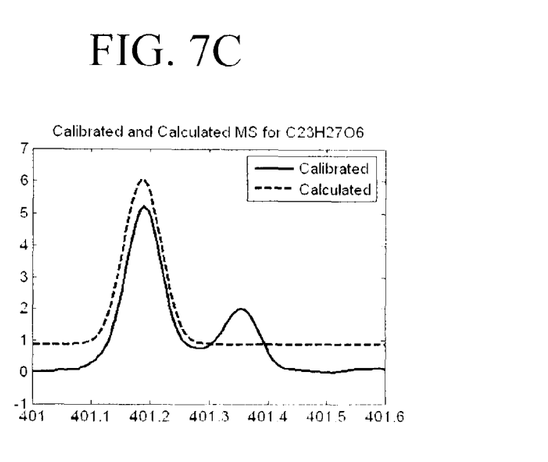
Figure 7D:
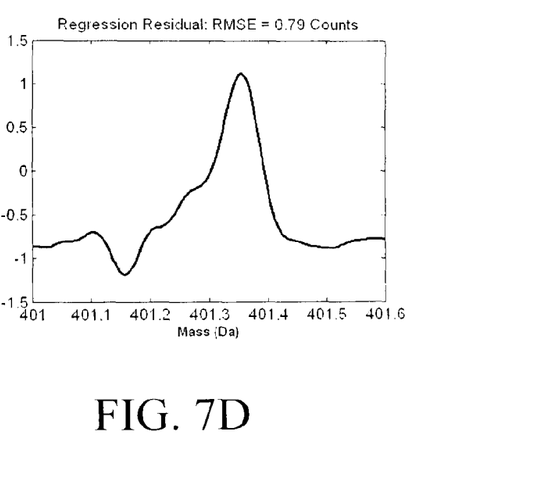

Referring to FIG. 6A, the measured mass spectrum after calibration is shown, along with the theoretically calculated mass spectrum from the top hit formula in FIG. 4, indicating a very close match, with regression residual shown in FIG. 6B with a RMSE of 0.42 counts. For the second hit in FIG. 4 shown in FIG. 6C, while the spectral match is visually similar, the residual and RMSE in FIG. 6D shows a significant increase.

FIGS. 7A, 7B, 7C and 7D show the same graphs as in FIGS. 6A, 6B, 6C and 6D, but on a much finer scale centered around the M+2 peak. It is now clear that the top hit has a much better fit than the $2^{nd}$ hit which has a displaced baseline due to the incorrect composition causing subtle differences in the isotope distribution.

The descriptions presented above process mass spectral data to obtain elemental composition by assuming that all involved elements in the formula are naturally occurring with each of their elemental isotope distribution given. Conversely, with known mass spectral data and given elemental composition (i.e., formula), it is possible to back calculate the elemental isotope distribution for at least one of its elements, thus providing an easy way for the determination of various isotopes and the relative abundances, such as isotope ratios for a given element.

Figure 8:
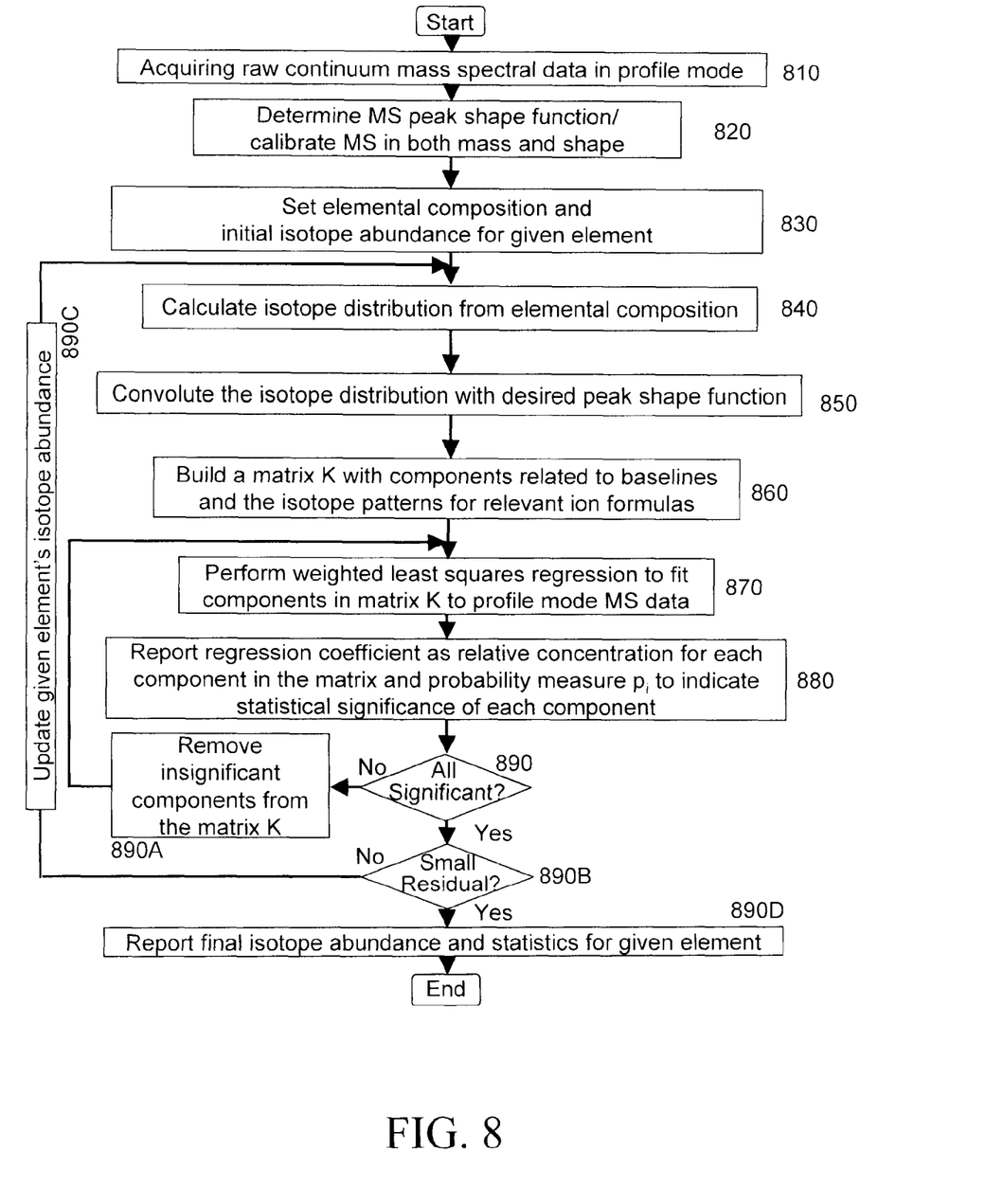
FIG. 8 is another possible flow chart of the steps in the analysis used by the system of FIG. 1.

Referring to FIG. 8, at step 810, raw continuum mass spectral data is obtained for a sample containing the analyte of interest. While, as mentioned above, most commercial techniques utilize stick spectral data, it will be recognized that the use of the profile mode raw spectrum means that data is not lost due to a premature gross simplification of the features of the data. However, this raw spectrum has characteristics relating to instrument peak shape function, instrument resolution, and baseline variations due to spurious ions and neutral particles that may reach the detector. Further, there may be a mass dependence with respect to all of these potential factors. For example, there is an exponential decay of baseline displacement as a function of increasing m/z in a MALDI system, principally due to ions of the matrix material, some of which arrive at the detector, despite every attempt to reduce their presence.

At step 820, the raw data acquired in step 810 is subjected to a full calibration of the mass spectrometer based on internal and/or external standards so as to standardize the raw continuum data. This assures that the peaks are lined up at the proper m/z values, and that the shape of the peaks is properly defined and known mathematically. This is preferably accomplished by the procedure set forth in U.S. Pat. No. 6,983,213 and International Patent Application PCT/US2004/034618 filed on Oct. 20, 2004, the entire contents of which are incorporated herein by reference. Instead of a full mass spectral calibration, the peak shape function can be calculated and used in the following mass spectral search process, at the expense of reduced mass accuracy during the search.

At step 830, a section of the mass spectral data containing the ion of interest is selected, and its elemental composition and initial values for the isotope distribution or ratio for the given element are set (the true isotope distribution of which is to be determined). The naturally occurring isotope abundances for this element will typically serve as good initial values.

At step 840, a theoretically calculated isotope distribution can be obtained for the given elemental composition. For other elements except for the element of interest, the isotope abundances are already known in advance and will be directly used in the calculation of the ion's isotope distribution. For the element of interest, whose isotope distribution is to be determined, its most recent estimates including assumed initial values will be used. The theoretical isotope distribution of the ion can be calculated in the manner described in U.S. Pat. No. 6,983,213 and International Patent Application PCT/US2004/034618 filed on Oct. 20, 2004.

At step 850 the isotope distribution is convoluted with the peak shape function calculated or specified as the target peak shape function in the full mass spectral calibration, all given in step 820, to obtain a calculated isotope pattern (mass spectral continuum) for the candidate formula. As used herein, for this purpose, and for other purposes throughout this document, the term convolution may refer to matrix operations, or point by point operation in Fourier transform space, or any other type of convolution, filtering, or correlation, either of a traditional type, or not.

At step 860, a matrix K is generated to include known and sometimes mass-dependent baseline functions and the isotope pattern for the candidate formula. Examples of possible baseline functions include a flat line and several lower order terms such as linear or quadratic terms. The combination of these lower order terms can adequately compensate for an exponentially decaying baseline within a small mass spectral range, and help arrive at the computationally efficient linear solutions in step 870, though one may choose to incorporate the nonlinear terms explicitly and seek a nonlinear solution instead. Matrix K may optionally contain any other components interfering with the candidate isotope's pattern such as the isotope patterns from co-existing ions, including isotope labeled version of the same candidate ion or a general background from the sample matrix. To model the possible mass offset between r and components in K, the first derivatives of the components in K or the first derivative of the sample measurement r may also be included.

At step 870, a weighted least squares regression is performed to fit the components of the matrix generated in step 860 to the acquired and/or calibrated mass spectral spectrum data of step 820, in the form given in Equations 1-2.

At step 880, the regression coefficients (values in c) are reported out as the relative concentrations for components included in matrix K along with probability measures in the form of F-statistic, t-statistic or p-value as, for example, given in Equations 3-4.

At step 890, a statistical test based on t-statistic, p-value, or other measures such as F-statistic is performed to determine whether any or all of components included in the matrix K are significant. In this regard, the baseline may be treated in the analysis as if it is another compound found in the sample (in the data produced in step 820). If any component is insignificant, then branching to step 890A occurs, and this component is removed from the matrix K before the next iteration back to step 870 (and continuing on to steps 880 and 890). This process of first estimating the contribution of the possible components as part of an overall fit, followed by the removal of insignificant baseline components serves the purpose of unbiased correction of components including baselines, without unnecessarily introducing extra components into matrix K and Equation 1. Typically as more components are added to the matrix K, its conditioning would get worse, resulting in less precise estimation of concentrations and a worsening of other statistical confidence. However, by removing insignificant components in the process, the conditioning of the K matrix is improved, leading to more precise concentration estimates for c and higher statistical confidence. This iterative removal of some components at this point is optional.

When all insignificant components have been removed, at step 890B, a statistical test on the residual e (Equation 1) is performed to check and see if the current estimate of the given element's isotope distribution results in large residuals, in which case adjustments to the most recent estimate of the given element's isotope distribution may be made in step 890C before returning to step 840 for another iteration. This adjustment of the given element's isotope distribution can be made in a Simplex optimization fashion, with Gauss-Newton iteration, or other linear or nonlinear iterative processes well established in the field of numerical analysis. In the case of Gauss-Newton iteration, the matrix K in step 860 may include a partial derivative of the theoretical isotope distribution with respect to the unknown isotope abundance of a given element in order to calculate an incremental update to the initial isotope abundance value linearly through the subsequent regression in step 870. This partial derivative typically can be calculated numerically around the initial abundance value(s).

When all components are deemed significant with a minimized residual, process flow is through step 890D to report the final isotope abundance and associated statistical measures such as confidence interval etc. to complete the analysis process.

Figure 9:
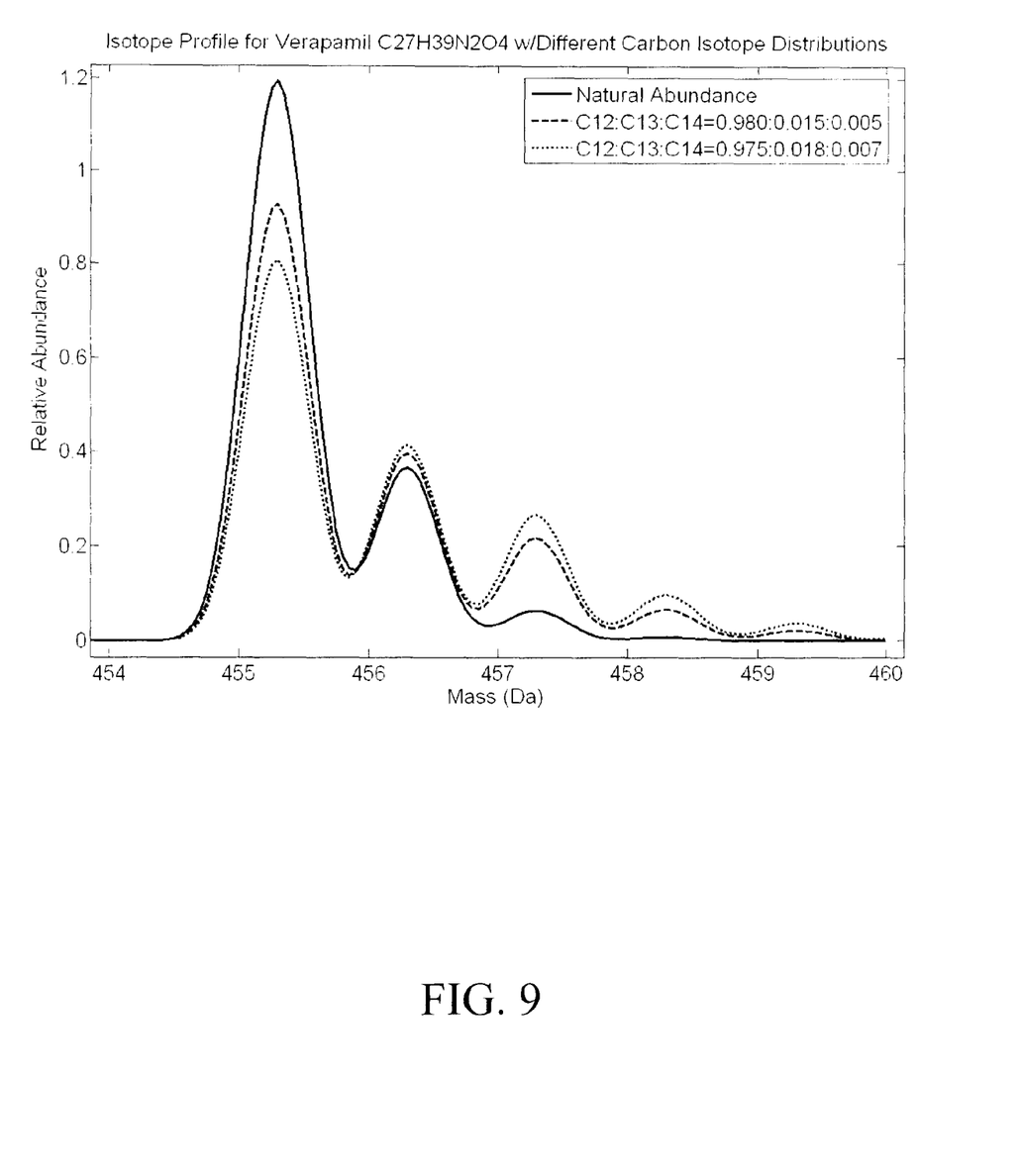
FIG. 9 is a graph showing the theoretical mass spectra profile for the same molecular formula with different carbon isotope distributions.

Referring to FIG. 9 where the theoretical isotope distributions for a small molecule drug, Verapamil ($C_{27}H_{39}N_2O_4^+$), are calculated for three slightly different carbon isotope abundances, one of which is naturally occurring carbon while the other two have slight variations in their carbon isotope abundances. It is clear from this simulation that there are significant and enough changes in the resulting isotope profile of the ion (even at unit mass resolution) to determine accurately the underlying isotope distribution for the carbon element.

For all the analysis described above, it may be advantageous to transform the m/z axis into another more appropriate axis beforehand, to allow for analysis with a uniform peak shape function in the transformed axis, as pointed out in U.S. Pat. No. 6,983,213 and International Patent Application PCT/US2004/034618 filed on Oct. 20, 2004.

The process described above includes a fairly comprehensive series of steps, for purposes of illustration, and to be complete. However, there are many ways in which the process may be varied, including leaving out certain steps, or performing certain steps before hand or "off-line". For example, it is possible to conduct a calibration once, and to use that calibration for some period of time with the same instrument. Furthermore, the operations performed on the peak components in matrix K need only be performed once, and the resulting peak components with a given target peak shape function may be used for all instruments or even instrument types that are fully calibrated to the same target peak shape function.

Conversely certain steps may be combined or performed at the same times as other steps. For example, if one or more known compounds or fragments are available as internal standards in the sample, which may be used to perform an on-the-fly full mass spectral calibration in the manner described in the U.S. Pat. No. 6,983,213 and International Patent Application PCT/US2004/034618 filed on Oct. 20, 2004.

It is noted that the terms "mass" and "mass to charge ratio (m/z)" are used somewhat interchangeably in connection with information or output as defined by the mass to charge ratio axis of a mass spectrometer. In cases where the ions observed are of multiple charges, the exact same process can be applied utilizing the invention outlined here, except that the term "mass" would mean "m/z" when referring to accurate mass, exact mass, isotope distribution, and isotope pattern. Similarly, the term "elemental composition" and "formula" are used interchangeably to refer to the chemical composition of analyte under measurement. These are common practices in the scientific literature and in scientific discussions, and no ambiguity will occur, when the terms are read in context, by one skilled in the art. The term accurate mass typically refers to a mass measurement that is more accurate than nominal mass, and represents a better approximation to theoretical, true mass, also commonly called exact mass.

The methods of analysis of the present invention can be realized in hardware, software, or a combination of hardware and software. Any kind of computer system—or other apparatus adapted for carrying out the methods and/or functions described herein—is suitable. A typical combination of hardware and software could be a general purpose computer system with a computer program that, when being loaded and executed, controls the computer system, which in turn control an analysis system, such that the system carries out the methods described herein. The present invention can also be embedded in a computer program product, which comprises all the features enabling the implementation of the methods described herein, and which—when loaded in a computer system (which in turn controls an analysis system), is able to carry out these methods.

Computer program means or computer program in the present context include any expression, in any language, code or notation, of a set of instructions intended to cause a system having an information processing capability to perform a particular function either directly or after conversion to another language, code or notation, and/or reproduction in a different material form. Thus the invention includes an article of manufacture, which comprises a computer usable medium having computer readable program code means embodied therein for causing a function described above. The computer readable program code means in the article of manufacture comprises computer readable program code means for causing a computer to effect the steps of a method of this invention. Similarly, the present invention may be implemented as a computer program product comprising a computer usable medium having computer readable program code means embodied therein for causing a function described above. The computer readable program code means in the computer program product comprising computer readable program code means for causing a computer to effect one or more functions of this invention. Furthermore, the present invention may be implemented as a program storage device readable by machine, tangibly embodying a program of instructions executable by the machine to perform method steps for causing one or more functions of this invention.

It is noted that the foregoing has outlined some of the more pertinent objects and embodiments of the present invention. The concepts of this invention may be used for many applications. Thus, although the description is made for particular arrangements and methods, the intent and concept of the invention is suitable and applicable to other arrangements and applications. It will be clear to those skilled in the art that other modifications to the disclosed embodiments can be effected without departing from the spirit and scope of the invention. The described embodiments ought to be construed to be merely illustrative of some of the more prominent features and applications of the invention. Thus, it should be understood that the foregoing description is only illustrative of the invention. Various alternatives and modifications can be devised by those skilled in the art without departing from the invention. Other beneficial results can be realized by applying the disclosed invention in a different manner or modifying the invention in ways known to those familiar with the art. The embodiments has been provided as an example and not as a limitation. Accordingly, the present invention is intended to embrace all alternatives, modifications and variances, including, but not necessarily limited to, those which fall within the scope of the appended claims.

What is claimed is:

1. A method for determining elemental composition of ions from mass spectral data, comprising the steps of:
    obtaining at least one accurate mass measurement from mass spectral data obtained by using a mass spectrometer;
    obtaining a search list of candidate elemental compositions whose exact masses fall within a given mass tolerance range from said accurate mass;
    reporting a probability measure based on a mass error;
    calculating, using a computer, an isotope pattern for each candidate elemental composition from said search list;
    constructing a peak component matrix including at least one of said isotope pattern and mass spectral data;
    performing a regression against at least one of isotope pattern, mass spectral data, and the peak component matrix;
    reporting a second probability measure for at least one candidate elemental composition based on said isotope pattern regression; and
    combining the two said probability measures into an overall probability measure through the use of probability multiplications.

2. The method of claim 1, where the isotope pattern has a desired peak shape function.

3. The method of claim 2, where the desired peak shape function is one of assumed peak shape function, actual peak shape function as one of measured and calculated, and target peak shape function.

4. The method of claim 2, where the isotope pattern is a linear combination of at least two ions.

5. The method of claim 4, where the at least two ions include native and isotope labeled versions of the ion.

6. The method of claim 1, where the measured mass spectral response has been calibrated to have a desired peak shape function.

7. The method of claim 6, where a desired peak shape function is one of assumed peak shape function, actual peak shape function as one of measured and calculated, and target peak shape function from a mass spectral calibration involving peak shape.

8. The method of claim 1, where the isotope pattern is theoretically calculated through the convolution of isotope distribution and a desired peak shape function.

9. The method of claim 8, where a desired peak shape function is one of assumed peak shape function, actual peak shape function as one of measured and calculated, and target peak shape function from a mass spectral calibration involving peak shape.

10. The method of claim 8, where the isotope distribution is theoretically calculated from at least one elemental composition.

11. The method of claim 8, where an elemental composition is obtained through a search of possible elemental compositions using the measured mass spectral response.

12. The method of claim 1, where the peak component matrix contains baseline components which are at least one of linear and nonlinear in nature.

13. The method of claim 1, where the peak component matrix contains first derivative of at least one of the measured mass spectral response and an isotope pattern already included in the peak component matrix.

14. The method of claim 1, where the peak component matrix contains at least one of the isotope pattern and its first derivative of any interfering ions.

15. The method of claim 1, where the regression is a multiple linear regression.

16. The method of claim 1, where the regression is a weighted regression.

17. The method of claim 16, where the weights are all ones.

18. The method of claim 16, where the weights are inversely proportional to the mass spectral variance.

19. The method of claim 18, where the mass spectral variance is proportional to the mass spectral intensity.

20. The method of claim 1, where the probability measure is a p-value.

21. The method of claim 1, where an overall p-value is derived as the product of two independent p-values.

22. The method of claim 21, where all candidate elemental compositions in said search list are ranked based on said overall probability measure.

23. The method of claim 1, where an estimated standard deviation is reported for said accurate mass measurement.

24. The method of claim 1, where the mass tolerance range is derived as a function of an estimated standard deviation in the accurate mass measurement.

25. The method of claim 1, where said probability measure based on mass error is established based on estimated standard deviation of the accurate mass measurement.

26. The method of claim 1, where the peak component matrix is updated and regression repeated by adding or deleting components in the matrix.

27. The method of claim 26, where adding or deleting components is based on probability measures obtained from a regression.

28. The method of claim 1, where a mass axis has been transformed through one of linear and nonlinear functions.

29. A computer programmed with non-transitory computer code for performing the method of claim 1.

30. The computer of claim 29, in combination with a mass spectrometer for obtaining mass spectral data to be analyzed by said computer to determine elemental composition of ions from said mass spectral data.

31. A non-transitory computer readable medium having computer readable instructions stored therein for causing a computer processor to perform the method of claim 1.

32. A mass spectrometer having associated therewith a computer for performing data analysis functions of data produced by the mass spectrometer, the computer performing the method of claim 1 to determine elemental composition of ions from said mass spectral data.

33. A method for determining elemental isotope ratios directly from mass spectral data, comprising the steps of:
   obtaining measured mass spectral response, said measured mass spectral response obtained by using a mass spectrometer;
   specifying the elemental composition of a given ion;
   specifying the initial isotope ratios for a given element in the ion;
   calculating, using a computer, the isotope pattern for said ion;
   constructing a peak component matrix including at least one of said isotope pattern and measured mass spectral response;
   performing a regression between measured mass spectral response and the peak component matrix; and
   reporting a regression residual and repeating the isotope pattern calculation, peak component construction, and regression process with updated isotope ratios to minimize this residual.

34. The method of claim 33, where the isotope pattern has a desired peak shape function.

35. The method of claim 34, where the desired peak shape function is one of assumed peak shape function, actual peak shape function as one of measured and calculated, and target peak shape function.

36. The method of claim 33, where the measured mass spectral response is calibrated to have a desired peak shape function.

37. The method of claim 36, where a desired peak shape function is one of assumed peak shape function, actual peak shape function as one of measured and calculated, and target peak shape function from a mass spectral calibration involving peak shape.

38. The method of claim 33, where the isotope pattern is theoretically calculated through the convolution of isotope distribution and a desired peak shape function.

39. The method of claim 38, where a desired peak shape function is one of assumed peak shape function, actual peak shape function as one of measured and calculated, and target peak shape function from a mass spectral calibration involving peak shape.

40. The method of claim 33, where the peak component matrix contains baseline components which are at least one of linear and nonlinear in nature.

41. The method of claim 33, where the peak component matrix contains first derivative of at least one of the measured mass spectral response and an isotope pattern already included in the peak component matrix.

42. The method of claim 33, where the peak component matrix contains at least one of the isotope pattern and its first derivative of any interfering ions.

43. The method of claim 33, where the regression is a multiple linear regression.

44. The method of claim 33, where the regression is a weighted regression.

45. The method of claim 44, where weights for the regression are all ones.

46. The method of claim 44, where weights for the regression are inversely proportional to the mass spectral variance.

47. The method of claim 46, wherein mass spectral variance is proportional to mass spectral intensity.

48. The method of claim 33, where the peak component matrix is updated and regression repeated by adding or deleting components in the matrix.

49. The method of claim 48, where adding or deleting components is based on probability measures obtained from a regression.

50. The method of claim 33, where a mass axis has been transformed through one of linear and nonlinear functions.

51. A computer programmed with non-transitory computer code for performing the method of claim 33.

52. The computer of claim 51, in combination with a mass spectrometer for obtaining mass spectral data to be analyzed by said computer to determine elemental isotope ratios from said mass spectral data.

53. A non-transitory computer readable medium having computer readable instructions stored therein for causing a computer processor to perform the method of claim 33.

54. A mass spectrometer having associated therewith a computer for performing data analysis functions of data produced by the mass spectrometer, the computer performing the method of claim 33 to determine elemental isotope ratios from said mass spectral data.

* * * * *